United States Patent [19]

Hashemi et al.

[11] Patent Number: 5,631,246
[45] Date of Patent: May 20, 1997

[54] USE OF PAF

[75] Inventors: Sofia Hashemi, Ottawa; Douglas Palmer, Hull, both of Canada

[73] Assignee: The Canadian Red Cross Society, Ottawa, Canada

[21] Appl. No.: 31,573

[22] Filed: Mar. 15, 1993

[51] Int. Cl.$^6$ .................................................. A61K 31/66
[52] U.S. Cl. .......................................... 514/114; 514/120
[58] Field of Search ............................ 514/136, 114, 514/120

[56] References Cited

U.S. PATENT DOCUMENTS 5,091,363  2/1992  Heimburger et al. .................. 514/2

OTHER PUBLICATIONS

Camussi et al., J Immunol 131(5):2397–2403 (1983).
Tranquille et al., Eur J Pharmacol 213(2):285–292 (1992).
Tranquille et al., Thromb Haemostasis 66(4):479–483 (1991).
Tranquille et al. J Cardiovasc Pharmacol 18(1):35–42 (1991).
Tranquille et al., Thromb Haemostasis 63(3):454–8 (1990).
The Merck Manual of Diagnosis & Therapy, 16th ed., Merck & Co, Rahway, NJ 1992.
Braquet, P., and D. Hosford, (1991) "Ethnopharmacology and the Development of Natural PAF Antagonists as Therapeutic Agents", Journal of Ethnopharmacology 32:153–139.
Hanahan, D.J., (1986) "Platelet Activating Factor: A Biologically Active Phosphoglyceride", Ann. Rev. Biochem. 55:483–509.
Heller, R., et al., (1992) "Human Endothelial Cells Are Target For Platelet–Activating Factor", J. Immunology 149(11):3682–3688.
Hwang, S., (1991) "Function and Regulation of Extracellular and Intracellular Receptors of Platelet Activating Factor", Annals of the New York Academy of Sciences 629:217–226.
O'Flaherty, J.T. and R.L. Wykle, (1989) "PAF and Cell Activation", Frontiers in Pharmacology and Therapeutics: Platelet Activating Factor and Human Disease, Blackwell Scientific Publications, chapter 5, pp. 117–137.
Prescott, S.M. et al., (1984) "Human Endothelial Cells in Culture Produce Platelet–Activating Factor (1–alkyl–2–acetyl–sn–glycero–3–phosphocholine) When Stimulated With Thrombin", Proc. Natl. Acad. Sci. USA 81:3534–3538.
Prescott, S.M., et al., (1990) "The Role of Platelet–Activating Factor in Endothelial Cells", Thrombosis and Haemostasis 64(1):99–103.
Rola–Pleszczynski, M., (1990) "Priming of Human Monocytes with PAF Augments Their Production of Tumor Necrosis Factor", Journal of Lipid Mediators 2:s77–s82.
Snyder, F., (1987) "Composition of Alkyl Ether–Linked Phospholipids in Mammalian Tissues", Platelet–Activating Factor and Related Lipid Mediators, Plenum Press, chapter 3, pp. 55–85.
Snyder, F., (1990) "Platelet–Activating Factor and Related Acetylated Lipids as Potent Biologically Active Celullar Mediators", Am. J. Physiol. 259(Cell Physiol. 28):C697–C708.
Vargaftig, B.B., et al., (1981) "Background and Present Status of Research on Platelet–Activating Factor (PAF–Acether)", Annals New York Academy of Sciences, 370:119–137.
Whatley, R.E., et al., (1987) "Production of Platelet–Activating Factor by Endothelial Cells", Seminars in Thrombosis and Hemostasis 13(4):445–453.
Zimmerman, G.A., et al., (1990) "Endothelial Cells for Studies of Platelet–Activating Factor and Arachidonate Metabolites", Methods In Enzymology 187:520–535.

Primary Examiner—Michael G. Wityshyn
Assistant Examiner—Jean C. Witz
Attorney, Agent, or Firm—Browdy and Neimark

[57] ABSTRACT

The use of platelet-activating factor (PAF) to increase the levels of von Willebrand factor and/or Factor VIII in blood is disclosed. The use of PAF has particular application in the treatment of von Willebrand disease and haemophilia A.

16 Claims, 5 Drawing Sheets

USE OF PAF

BACKGROUND OF INVENTION

The invention relates to the novel use of PAF to increase von Willebrand factor and/or Factor VIII in blood. One specific application is in the treatment of von Willebrand disease and of haemophilia A.

Haemophilia A is a sex linked bleeding disorder characterized by deficiency in factor VIII. Von Willebrand disease is a bleeding disorder characterized by deficiency in von Witlebrand factor (also referred to as vWf). While factor VIII is one of the essential proteins involved in the blood coagulation cascade, von Willebrand is a glycoprotein whose function in injury repair is limited to blood vessels. Von Willebrand factor causes platelet adhesion to the site of the. vascular injury.

The conventional treatments for both von Willebrand disease and haemophilia A have been the administration of von Willebrand factor and factor VIII respectively or the administration of DDAVP (1-deamino-8-D-arginine vasopressin), a synthetic vasopressin analogue or of AVP (arginine vasopressin) analogues or DDAVP analogues. The use of blood plasma containing factor VIII and/or von Willebrand factor has several disadvantages, one being the risk of acquiring infectious diseases such as hepatitis B, hepatitis C and HIV associated with the use of blood products and the fact that the concentration of factor VIII and von Willebrand factor in blood is very low.

The drawbacks associated with the use of blood products in the treatment of blood disorders led to the use of DDAVP. DDAVP has been found to increase the plasma concentration of von Willebrand factor and factor VIII in patients with mild or moderate haemophilia A or von Willebrand disease and in normal individuals. In spite of the widespread use of DDAVP, its molecular mechanism of action has not been completely elucidated.

There are also a number of patents disclosing various agents for the treatment of haemophilia A and/or other bleeding disorders. By way of example, U.S. Pat. No. 5,171,844 issued on Dec. 15, 1992 discloses the use of derivatives and fragments of factor VIII for the treatment of haemophilia A. U.S. Pat. No. 5,091,363 issued on Feb. 25, 1991 discloses the use of a mixture comprising factor VIII, antithrombin III, phospholipid and calcium ions as well as factor IX for the treatment of haemophilia A. U.S. Pat. No. 5,180,583 issued on Jan. 19, 1993 discloses the use of a composition comprising factor VIIA for the treatment of von Willebrand disease while U.S. Pat. No. 4,501,731 issued on Feb. 26, 1985 discloses the use of factor X zymogen for the treatment of various bleeding disorders.

SUMMARY OF THE INVENTION

In a broad embodiment, the present invention relates to the use of PAF and PAF analogues to increase the levels of von Willebrand factor and/or Factor VIII in blood. In another embodiment, the invention relates to the use of PAF for the treatment of von Willebrand disease and haemophilia A.

BRIEF DESCRIPTION OF THE DRAWINGS:

FIG. 1A shows the % vWf release from ECs exposed for 4 hours to supernatants from monocytes treated with 0 or 100 ng DDAVP/mL (0 and 84.5 nM) for 30 minutes; P<0.001 by paired Students's t-test. FIG. 1B shows PAF release from monocytes exposed to 0 or 100 ng DDAVP/mL for 30 minutes; P<0.001 by paired t-test.

FIG. 7A: 0 ng DDAVP/mL (Δ) vs. 100 ng DDAVP/mL (▲). From the ANOVA for the effect of time at 0 ng DDAVP/mL: F=7.27, P<0.001 and at 100 ng DDAVP/mL: F=16.93, P<0.001. FIG. 7B: 0 ng DDAVP/mL (○) vs. 100 ng DDAVP/mL (●). From the ANOVA for the effect of time; F=19.6, P<0.001 (0 ng DDAVP/mL) and F=21.39, P<0.001 (100 ng DDAVP/mL).

DETAILED DESCRIPTION

Figure 1A:
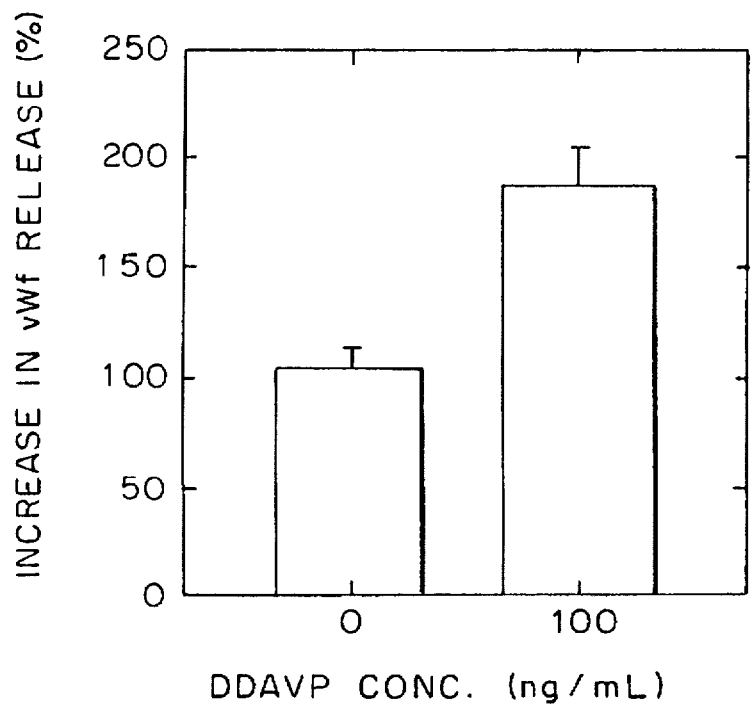
FIGS. 1A and 1B shows the effect of DDAVP on the secretion of von Willebrand factor releasing factor and PAF from monocytes (n=26).

In accordance with the present invention, a novel use for PAF has been discovered. As mentioned above, one of the preferred modes of treatment of mild or moderate forms of haemophilia A or von Willebrand disease has been the use of DDAVP or 1-deamino-8-D-arginine vasopressin. It has been established that DDAVP causes an increase in the plasma concentration of von Willebrand factor as well as factor VIII in vivo (Mannucci et al. (1975) Mechanism of Plasminogen Activator and Factor VIII Increase After Vasoactive Drugs, Br. J. Haematol., 30:81–93; Mannucci et al. (1981) Response of Factor VIII/Von Willebrand Factor to DDAVP in Healthy Subjects and Patients with Haemophilia A and Von Willebrand's Disease, Br. J. Haematol., 47:283–293 and Mannucci (1986) Desmopressin (DDAVP) for Treatment of Disorders of Hemostasis, In Progress of Hemostasis and Thrombosis, Vol. 8, B. S. Coller ed., Grune and Stratton, Orlando, Fla., pp. 19–45). DDAVP has also been given to healthy donors to increase plasma levels of Factor VIII and vWf prior to donation resulting in significant increases in the potency and purity of Factor VIII/vWf recovered after commercial plasma fractionation (Mannucci (1988) Desmopressin: A Nontransfusional Form of Treatment for Congenital and Acquired Bleeding Disorders, Blood, 72:1449–1455; Bolan et al. (1990) Pharmacologic Agents in the Management of Bleeding Disorders, Transfusion, 30:541–551).

In spite of the widespread use of DDAVP, its molecular mechanism of action has not been completely elucidated. It was found that while vWf levels increased following DDAVP treatment in vivo, there was no increased secretion of vWf by endothelial cells in vitro following DDAVP treatment, thus suggesting that some intermediary factor secreted from other cells was involved (Hashemi et al. (1990) DDAVP-Induced Release of Von Willebrand Factor from Endothelial Cells In Vitro: The Effect of Plasma and Blood Cells, Biochem Biophys. Acta, 1052:63–70; Mannucci (1986). supra; Moffat et al. (1984) The Effect of Deamino-D-Arginine Vasopressin (DDAVP) and Naloxone Infusion on Factor VIII and Possible Endothelial Cell Related Activities, Br. J. Haematol., 57:651; Booyse et al. (1981) Effects of Various Agents on Ristocetin-Willebrand Factor Activity in Long-Term Cultures of Von Willebrand and Normal Human Umbilical Vein Endothelial Cells, Thromb. Haemostas., 46:668; Tuddenham et al. (1981) Synthesis and Release of Factor VIII by Cultured Human Endothelial Cells, Br. J. Haematol., 47:617; Hashemi et al. (1990). supra; Barnhardt et al. (1983). DDAVP:Does the Drug Have a Direct Effect on the Vessel Wall?, Thromb. Res. 31:239; Booth et al. (1987) An In Vitro Model for the Study of Acute Release of Von Willebrand Factor From Human Endothelial Cells, Br. J. Haematol. 67:71). It had been found that one of the target cells for DDAVP were monocytes and that they secreted some factor or factors, which following addition to EC cultures enhanced the release of vWf (Hashemi et al. (1990), supra). As a result of further studies conducted by the present inventors, it was discovered that PAF was the intermediary involved in the DDAVP mechanism of action.

PAF or platelet activating factor is also known as 1-O-alkyl-2-acetyl-sn-glycerol-3-phosphocholine or 1-O-alkyl-2-acetyl-sn-glyceryl-3-phosphorylcholine and has the following formula:

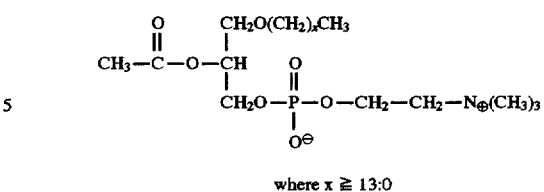

where x ≥ 13:0

The $C_{16}{}^a$ or $C_{18}{}^b$ forms are the most common forms of PAF in nature and are known as:

a) 1-O-hexadecyl-2-acetyl-sn-glycero-3-phosphocholine (or $C_{26}H_{54}NO_7P$); and b) 1-O-octadecyl (or stearyl)-2-acetyl-sn-glycero-3-phosphocholine (or $C_{28}H_{58}NO_7P$).

Platelet activating factor is also known by a number of other acronyms including PAF-acether, AGEPC (or acetylglycerylether-phosphorylcholine) and APRL (or antihypertensive polar reno-medullary lipid). The acronym PAF will be used throughout the present specification.

PAF is a very potent lipid mediator known to stimulate a wide span of biological responses ranging from aggregation and degranulation of platelets and activation of neutrophils to a variety of cellular effects involving the stimulation of chemotaxis, chemokinesis, superoxide formation, protein phosphorylation, activation of protein kinase C, arachidonic acid and phosphoinositide metabolites, glycogenolysis and tumour necrosis factor production. PAF has been considered to be a key component in numerous diseases related to hypersensitivity and inflammatory responses (Snyder (1990) Platelet-Activating Factor and Related Acetylated Lipids as Potent Biologically Active Cellular Mediators, Am. J. Physiol. 259:C697).

In the examples that follow, the following experimental protocols were used:

Experimental Protocols

1. DDAVP, THROMBIN AND PAF DDAVP (1,500 µg/mL; Ferring AB, Malmo, Sweden), purified human thrombin and PAF (Sigma Chemical Co., St. Louis, Mo.) were diluted in DMEM/F12+1% Nutridoma-HU as required. Synthetic PAF (1-O-alkyl-2-acetyl-sn-glyceryl-3-phosphorylcholine; Sigma #P-9525) prepared from bovine heart lecithin (Demopoulos et al. (1979) J. Biol. Chem. 254: 9355–358) was 99% pure by TLC analysis, HPLC analysis indicated this product consisted of 70% $C_{16}$ and 13% $C_{18}$ forms of PAF (Mita et al., (1989) Anal. Biochem. 180:131–135). After removal of chloroform, PAF was resuspended in DMEM/F12 culture medium containing 1% Nutridoma-HU (final protein concentration of 40 µM stock solution). After sonication for 3×1 minute periods, the PAF solution was diluted and used immediately. Conditioned media (or supernatants) from untreated or DDAVP-treated monocytes were either incubated directly with ECs or incubated with ECs after lipid extraction and reconstitution in fresh media.

2. ECs (endothelial cells)

Immediately prior to stimulation, second passage ECs were washed 3×with DMEM/F12+1% Nutridoma-HU and then incubated at 37° C. for 4 hours, except where otherwise noted, with either fresh media±agonists, supernatants from DDAVP-treated or untreated monocytes in a $CO_2$ incubator. Media with or without thrombin (@5 units/mL) served as positive and negative controls respectively. ECs were incubated for 1, 10, 20 or 30 minutes and 1, 2, 4, 6 and 24 hours in the PAF and thrombin time course studies. The EC conditioned media were recovered, centrifuged to remove any cell debris, and then frozen at −80° C. for a maximum period of 4 weeks prior to analyses. For experiments with PAF receptor antagonist, ECs were incubated with PAF (100 or 300 pM) or thrombin or supernatants from untreated or DDAVP-treated monocytes in the absence or presence of 10 μM BTP-dioxolane. Where appropriate ECs were preincubated with BTP-dioxolane which was not cytotoxic to the cells as determined by the dye exclusion test.

EXAMPLE 1

Effects of DDAVP on the Release of Cytokines by Monocytes

In an attempt to elucidate the mechanism of action of DDAVP, the effect of DDAVP on cytokines was monitored. Cytokines such as IL-1β, TNF-α, IL-6, and colony-stimulating factors are produced by monocytes after exposure to a variety of agonists (Molvig et al. (1988) Scand. J. Immunol. 27:705–716; Lu et al. (1988) Blood 72:34–41; Tosato and Jones (1990) Blood 75:1305–1310). Moreover, cytokines have been shown to induce vWf release from ECs (Giddings and Scholl (1987) Thromb. Res. 47:259–267; Schorer et al. (1987) Br. J. Haematol. 67:193–197; Hashemi et al. (1990) supra). To evaluate whether or not various cytokines are released from monocytes following exposure to DDAVP, purified human monocytes were incubated with medium alone or with 100 ng DDAVP/mL (84.5 nM) for 30 minutes, and the amount of different cytokines in the monocyte supernatants were measured.

In order to conduct this experiment endothelial cells, mononuclear cells and monocytes were isolated. The methods used in the isolation of these cells and the cytokine assays are set out below:

a) Umbilical vein endothelial cell cultures

Endothelial cells (ECs) were harvested from human umbilical cord vein as described by Jaffe et al. ((1973) Culture of Human Endothelial Cells Derived from Umbilical Veins: Identification by Morphologic and Immunologic Criteria, J. Clin. Invest. 52:2745–2756) and modified by Hashemi et al. (1990, supra). Endothelial cells were subcultured in 0.2% (w/v) gelatin-coated, 12-well Linbro™ polystyrene, tissue culture plates (Flow Laboratories, Mississauga, Ontario), then plated at a density of 1–2×10$^4$/well and grown to confluence.

b) Preparation of mononuclear cells (MNC)

Peripheral blood MNC were isolated from one unit of CPDA-1 blood collected from normal donors. Following centrifugation at 300×g for 15 minutes at 20° C., the top layer of plasma was recovered and respun at 2,000×g for 15 minutes to provide cell-free autologous plasma. The remaining plasma and buffy coat were resuspended, adjusted to 35 mL per 60 mL volume of whole blood with PBS (Dulbecco's phosphate buffered saline-Gibco BRL), and layered over 12 ml of Histopaque 1077 (Sigma). The MNC recovered by centrifugation at 300×g for 30 minutes were washed 3×in PBS+5% (v/v) fetal calf serum (FCS; Flow Laboratories, McLean, Va.). The cell concentration was adjusted to 5×10$^6$/mL in RPMI+5% FCS and then added to the pretreated tissue culture plates described by Hashemi et al. (1990, supra).

c) Isolation of monocytes

The method of Freundlich and Avdolomic (1983, Use of Gelatin/Plasma Coated Flasks for Isolating Human Peripheral Blood Monocytes, J. Immunol. Methods, 62:31–37) as modified by Hashemi et al. (1990, supra) was used to purify monocytes from mononuclear cells. The mononuclear cell suspension (5×10$^6$ cells/mL) was incubated for 18–20 hours at 37° C. in a $CO_2$ incubator. The monocytes were harvested with 10 mM EDTA (Gibco Laboratories) in RPMI+5% FCS and following centrifugation were washed 3×in media and resuspended in serum-free medium (DMEM/F12, Gibco) containing 1% Nutridoma-HU (Boehringer-Mannheim Canada, Laval, Quebec). The recovered cells met morphological criteria for monocytes and were 90% positive for monocyte CD14 surface marker determined by direct immunofluorescence using fluorescent conjugated anti-Leu-M3 (CD14) monoclonal antiserum (Becton-Dickinson, Mountain View, Calif.). Cell viability was greater than 90% as determined by trypan blue dye exclusion (Gibco). Monocytes were adjusted to 10$^6$ cells/mL with serum-free medium containing DDAVP as required. Cell suspensions were incubated in sterile Petri dishes, previously coated with 2% gelatin for 1 hour at 37° C., for 30-minutes or for 1, 2, 4, 6 and 24 hours. Monocyte-conditioned media were centrifuged at 2,000×g for 15 minutes and frozen at −80° C. prior to incubation with the EC monolayer cultures. For some experiments, conditioned media were lipid extracted as described prior to the PAF radioimmunoassay below. The dried extracts were reconstituted with fresh DMEM/F12+ 1% Nutridoma-HU media, briefly sonicated and added to EC cultures.

d) Cytokine assays

Cytokines, IL-1β, IL-6, IL-8, TNF-α, GM-CSF, and G-CSF were quantitated by specific ELISA using human recombinant cytokines as standards. The Quantikine™ kits for measuring IL-1β, IL-6, IL-8, TNF-α and G-CSF were purchased from R & D Systems (Minneapolis, Minn.). The GM-CSF assay kit came from Genzyme Corp. (Boston, Mass.). The minimum detectable levels of cytokines were: 4.5 pg/mL (IL-1β), 3.5 pg/mL (IL-6), 4.7 pg/mL (IL-8), 4.8 pg/mL (TNF-α), 11.2 pg/mL (G-CSF) and 10.0 pg/mL (GM-CSF).

Results:

The results, shown in Table 1, indicate the DDAVP has no significant effect on the secretion of IL-1β, IL-6, TNF-α, IL-8, GM-CSF or G-CSF even though vWf release from ECs was significantly affected when supernatants from DDAVP-treated monocytes were incubated with ECs for 4 hours. The effect of the unknown vWf releasing factor on ECs was not diminished if the monocyte supernatants were heat-treated at either 68° C. or 80° C. for 1 hour suggesting the vWf releasing factor was non-proteinaceous (experiments not presented).

EXAMPLE 2

Effect of DDAVP on the Release of Other Candidate Mediators from Monocytes

Other monocyte products such as prostaglandins and adenosine nucleotides might serve as agonists in mediating the effect of DDAVP on vWf release from ECs. To assess whether or not the release of these compounds was enhanced following stimulation of monocytes with DDAVP, their concentrations were individually measured in supernatants after a 30 minute exposure of monocytes to media alone or DDAVP at 100 ng/mL (84.5 nM).

Prostaglandins $E_2$, $F_{2a}$, and $I_2$ (assayed as 6 keto-$PGF_{1a}$) were assayed using the iodinated or tritiated (for $PGF_{2a}$) kits purchased from Amersham Canada (Oakville, Ontario). ATP and ADP were assayed using the adenosine-5'-triphosphate bioluminescent kit from Sigma (St. Louis, Mo.). Prior to assay, ADP present in standards or in samples was converted to ATP (Holmsen et al. (1966) Anal. Biochem. 17:456–473; (1972) Anal. Biochem. 46:489–501). Luminescence was measured using a Lumi-Aggregometer (Chrono-Log Corp., Havertown, Pa.). As can be seen from Table 2, treatment of monocytes with DDAVP had no significant effect on the secretion of PGE2, PGF$_{2\alpha}$, or PGI$_2$ or on the secretion of ATP or ADP from monocytes.

EXAMPLE 3

Effect of DDAVP on PAF Secretion from Monocytes

PAF is a known mediator of inflammation with a wide range of biological activities (Vargaftig and Bourgain (1989) Platelet Activating Factor and Human Disease, P. J. Barnes, C. P. Page and P. M. Henson eds. Blackwell Scientific, Cambridge, Mass. pp.220–230). This bioactive lipid mediator is rapidly synthesized and released after stimulation of a number of different cell types including monocytes (Braquet and Rola-Pleszcynski (1987) Immunol. Today 8:345–352). Therefore, it was of interest to determine whether or not DDAVP enhanced the secretion of PAF from monocytes. Purified monocytes were incubated in growth medium without (0 ng/mL) or with DDAVP (100 ng/mL or 84.5 nM) for 30 minutes at 37° C. Aliquots of the supernatants from untreated or DDAVP-treated monocytes were added to EC culture for a period of 4 hours, and the vWf released from the ECs was assessed by enzyme-linked immunosorbent assay (ELISA) described by Hashemi et al. (1990, supra). The standard consisted of a pool of plasma from 20 normal individuals previously determined to contain 1 unit of vWf per mL by the procedure of Zimmerman et al. (1977, J. Clin. Invest. 59:984–989). The results are expressed as the % of vWf released above that released by ECs incubated in fresh culture media alone (e.g., [{vWf release from ECs exposed to agonists or to monocyte supernatants±DDAVP}—{vWf release from ECs exposed to fresh media alone}]/[vWf from ECs exposed to fresh media alone]×100%). For some experiments, the maximum vWf that could be released was determined. Following incubation, the EC conditioned media were recovered and fresh media containing 0.05% (v/v) Tween 20 and 10 μM each of the protease inhibitors D-phenylalanyl-phenylalanyl-arginyl-chloromethyl ketone, D-phenylalanyl-propyl-arginyl-chloromethyl ketone and 1,5-Dansyl-glutamyl-glycyl-arginyl-chloromethyl ketone were added to the EC monolayers of each corresponding well. The cells were freeze-thawed three times and, to assure complete breakdown of the cell membranes as well as the Weibel-Palade bodies, disrupted in a glass homogenizer using a motor-driven teflon pestle. After centrifugation, total vWf concentration was determined in the supernatants.

In addition, PAF was extracted from the monocyte supernatants and assayed using the following highly specific and sensitive radioimmunoassay. As the most predominant bioactive forms of PAF secreted by monocytes are the C$_{16}$ and C$_{18}$ alkyl moieties (Sugiura and Waku, (1987) Platelet-Activating Factor and Related Lipid Mediators, F. Snyder Ed. Plenum Press, N.Y. 55–85; Prescott et al. (1990) Proc. Natl. Acad. Sci. U.S.A. 81:3534–3538), PAF was quantitated using the highly specific and sensitive $^{125}$I-RIA kit manufactured by NEN Research Products (Du Pont Canada, Mississauga, Ontario, Canada) following extraction of the monocyte supernatants with 5 mL each of methanol and chloroform and 3.5 mL of water per mL of sample. The recovered chloroform layers, dried under nitrogen, were reconstituted in the PAF assay kit buffer prior to analysis. The development, specificity, and sensitivity of this assay for the C$_{16}$ and C$_{18}$ forms of PAF have been previously documented (Smal et al. (1989) Molec. Immunol. 26:711–719; (1990) J. Molec. Recognition 3:169–173; (1990) J. Immunol. Methods 128:183–188; (1990) J. Reprod. Fert. 90:419–425). Recoveries of PAF (90±1%, n=>130) were assessed by adding trace amounts of $^3$H-PAF to the sample prior to extraction and determining the % recoveries using a liquid scintillation counter (Model-7000, Beckman Instruments Canada). Iodinated samples were counted on a Beckman Gamma 5500 counter (Beckman Instruments, Fullerton, Calif.). The 3H-PAF (10 Ci/mmole) and $^{125}$I-PAF (2200 Ci/mmole) consisted of a 1:1 admixture of the C$_{16}$ and Cla forms of PAF. Repeated analysis of PAF in monocyte conditioned media stored at –80° C. for various periods of time gave the same values (within experimental error).

Figure 1B:
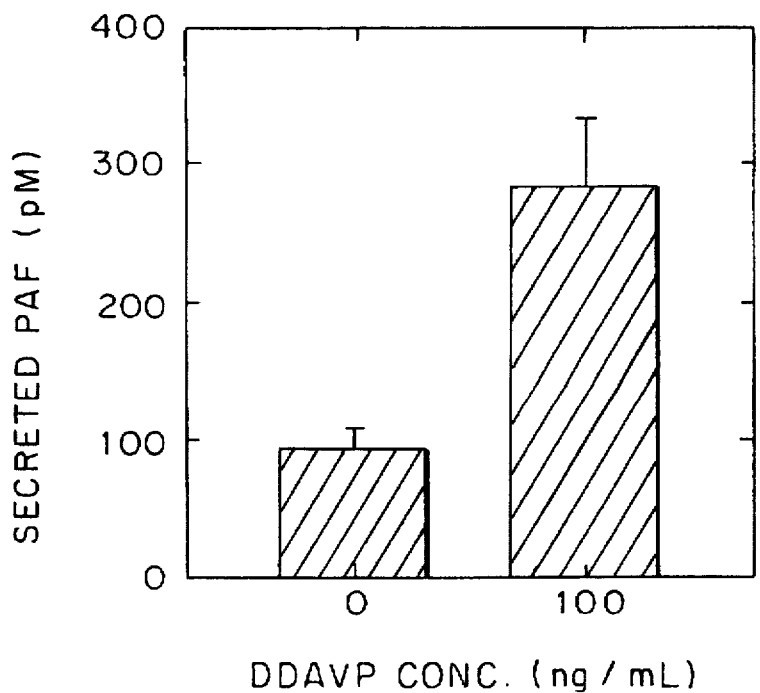
Figure 2:
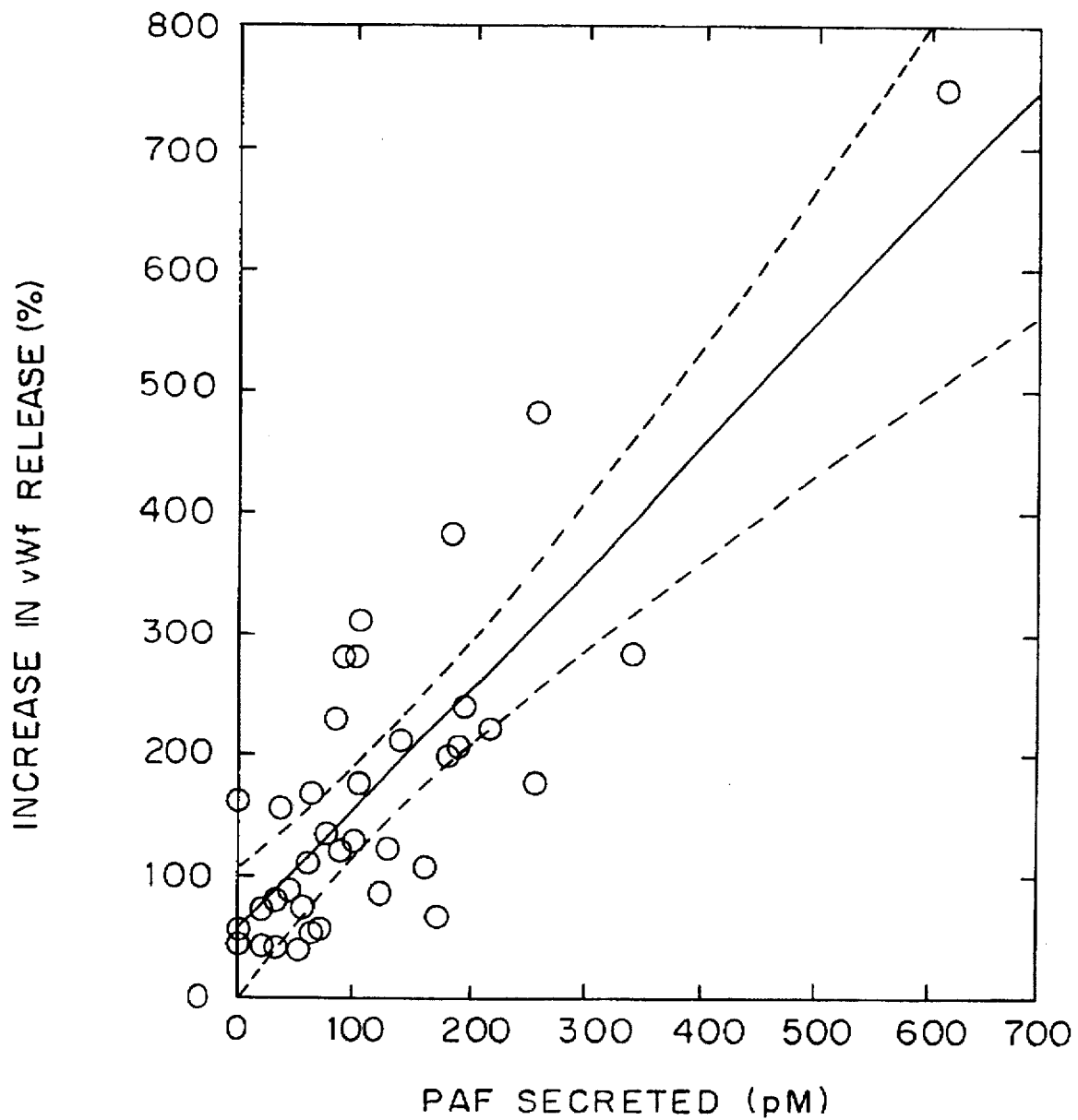
FIG. 2 shows the correlation between monocyte PAF secretion and endothelial cell (EC) release of von Willebrand factor. The correlation coefficient is 0.82 with a level of significance of P<0.001 (t-test). The dotted lines indicate the 99% confidence interval.
Figure 3:
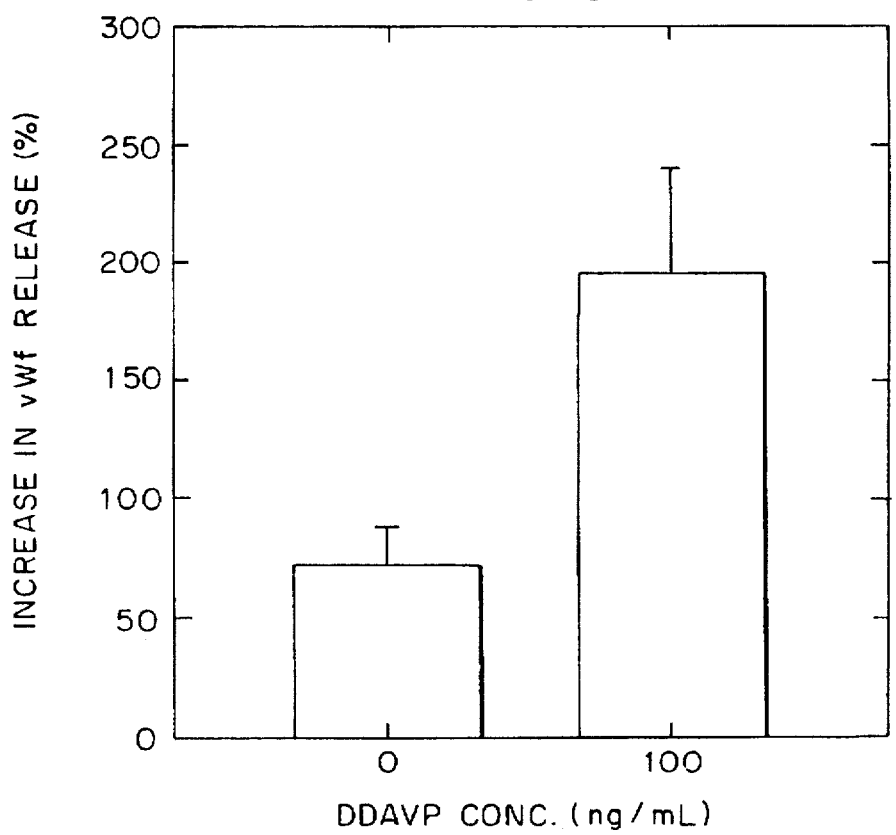
FIG. 3 shows the effect of lipid extracted supernatants from untreated or DDAVP treated monocytes on the release of von Willebrand factor from endothelial cells. Statistical analysis: 0 verus 100 ng DDAVP/mL: P<0.05 by paired t-test (n=7).

As shown in FIG. 1A, significant increases in vWf release from ECs were produced by supernatants from DDAVP-stimulated monocytes (186% cf. 104%; P<0.001). FIG. 1B shows that although monocytes not treated with DDAVP release low levels of PAF (94 pM), significantly greater PAF release was observed in the presence of 100 ng DDAVP/mL (284 pM; P<0.001). There was a positive correlation (FIG. 2) between PAF release from monocytes and vWf release from ECs (correlation coefficient=0.82, P<0.001). The effect of monocyte supernatants subjected to lipid extraction prior to reconstitution and incubation on vWf release from ECs is shown in FIG. 3. Extracts of the supernatants from untreated or DDAVP-treated monocytes enhanced the release of vWf from ECs by 71% and 195%, respectively (P<0.05) and were not significantly different than the responses observed using unextracted monocyte supernatants.

EXAMPLE 4

Effect of Purified PAF on vWf Release from ECs

Figure 4:
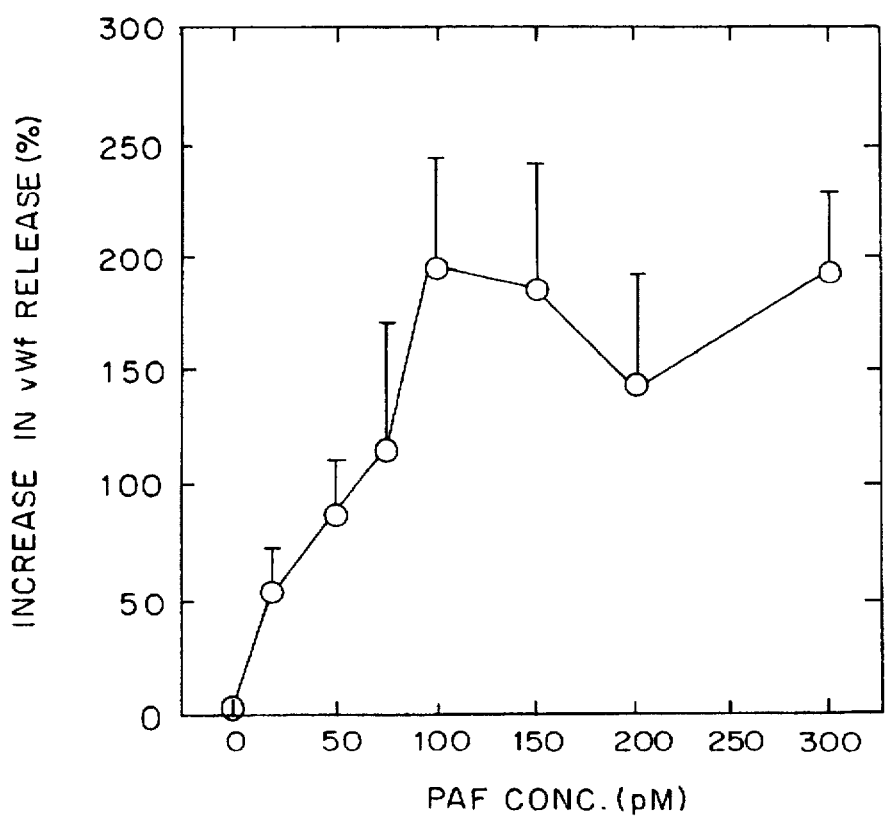
FIG. 4 shows the effect of PAF concentration on the release of von Willebrand factor from endothelial cells (n=5). Pure PAF was incubated with the EC monolayers as described in Materials and Methods. Statistical analyses: P<0.01 by ANOVA.
Figure 5:
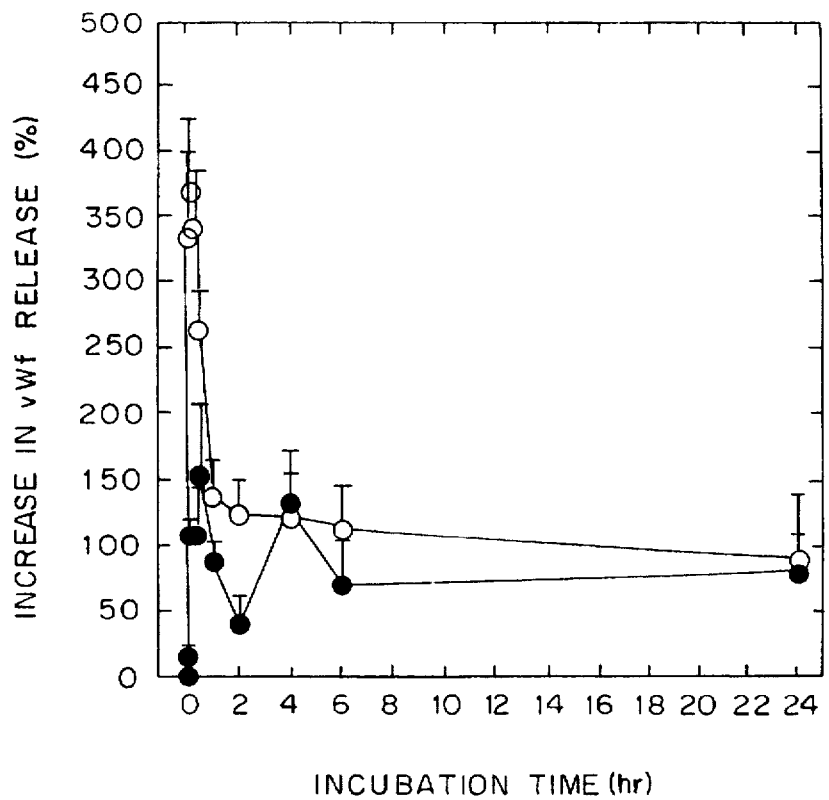
FIG. 5 shows the effect of incubation time on PAF or thrombin induced release of von Willebrand factor from endothelial cells (n=5). Monolayers ECs were exposed to media ±300 Pm PAF (●) or media ±5 units thrombin/ml (○) for various times as described in Materials and Methods. Statistical analyses: ANOVA for the effect of time within groups. PAF:F=2.112, P<0.05 or thrombin: F=11.34, P<0.001. T-test: 300 pM PAF at 30 minutes and 4 hours (P<0.05); thrombin at 1, 10, and 20 minutes (P<0.001), at 30 minutes (P<0.01), and at 1, 2, or 4 hours (P<0.05) as compared to ECs exposed to fresh media alone for an equivalent period of time (paired t-test).

In order to examine the responsiveness of ECs to direct PAF exposure, we incubated the monolayers of ECs with 0–300 pico molar (pM) PAF for a period of 4 hours at 37° C. and determined the amount of vWf released into the EC media. As shown in FIG. 4, PAF provoked the release of in the concentration range between 25 pM and 300 pM with the greatest response occurring in the range 100–300 pM. To determine the time course of PAF effects on vWf release, 300 pM PAF was incubated with monolayers of ECs for 1, 10, 20 and 30 minutes as well as for 1, 2, 4, 6 and 24 hours. FIG. 5 shows that ECs stimulated with PAF released vWf at all time points up to 24 hours. At 300 pM PAF, vWf release from ECs was maximal after 30 minutes (151%-P<0.05) with a reduced effect at later times. This represents ~4% of the maximal 3584% vWf recoverable from secreted and cell-associated vWf. As a control, the vWf release from thrombin stimulated ECs was also determined (FIG. 5). The optimal effect of thrombin on vWf release from ECs was observed by 10 minutes (368%; P<0.001) falling to 261% by 30 minutes, 137% by 1 hour, and remaining elevated after 24 hours (88%).

EXAMPLE 5

Time Course and Dose Response of PAF Release from Monocytes in Response to DDAVP In view of the enhanced levels of PAF observed in monocyte supernatants following DDAVP treatment, further studies were carried out to determine the effect of 10–800 ng DDAVP/mL on the secretion of PAF from monocytes (FIG.

6). A significant increase in the secretion of PAF from monocytes was observed at DDAVP concentrations from 100 to 800 ng/mL (84.5–676 nM). The data indicated that the maximum PAF secretion from monocytes of 480 fmoles/mL occurred at 200 ng DDAVP/mL (169 nM) after 30 minutes exposure with no further significant increases observed at higher concentrations of DDAVP. The ED50 for PAF secretion from monocytes was estimated to occur at 85 ng DDAVP/mL. When supernatants from these experiments were incubated with ECs for 4 hours at 37° C., significant increases in vWf release were observed at all concentrations tested. The maximum vWf release from ECs was obtained with supernatants from monocytes treated with 100 ng DDAVP/mL with an ED50 estimated to occur at 45 ng DDAVP/mL.

Figure 7A:
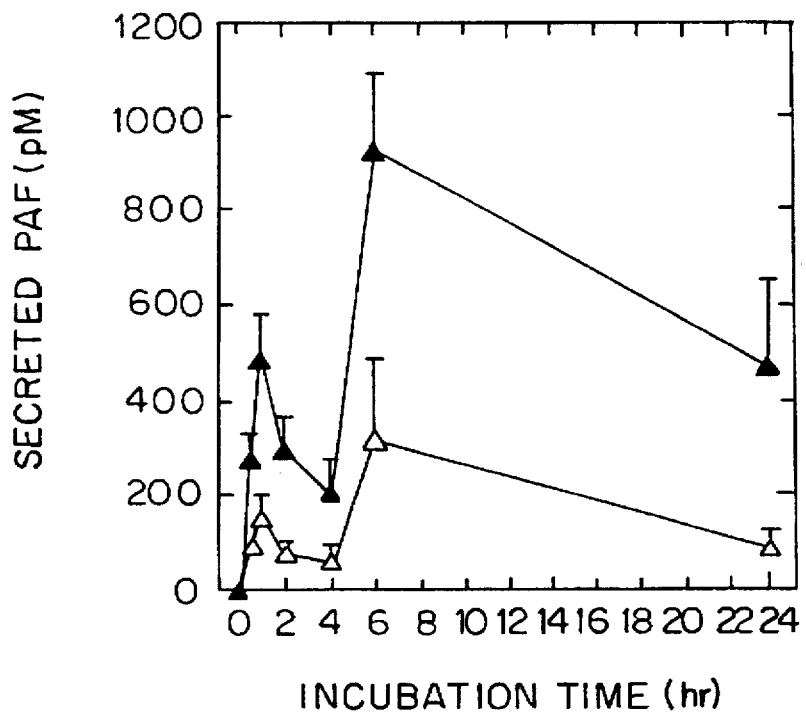
FIGS. 7A and 7B show the effect of incubation time on monocytes with 0 or 100 ng DDAVP/ml (84.5 nM) on the secretion of PAF (FIG. 7A) and von Willebrand factor (FIG. 7B) releasing factor from monocytes (n=5 or more experiments). Monocytes were exposed to the indicated concentrations of DDAVP for 30 minutes, 1 hr, 2 hr, 4 hr, 6 hr, and 24 hr. Aliquots of the monocyte conditioned media were then either assayed for PAF content or were incubated with ECs for a period of 4 hours to determined their effects on the release of vWf as described in Materials and Methods. Statistical analyses.

In further experiments, we followed the time course of PAF secretion from monocytes treated with 0 or 100 ng DDAVP/mL (FIG. 7A,B). After 30 minutes, an increase in PAF was observed in supernatants from DDAVP-treated monocytes with a further increase observed after 1 hour. However, PAF secretion declined sharply from 2–4 hours, increased again at 6 hours, and was still elevated after 24 hours. At any point in time, there were higher levels of PAF present in post-DDAVP monocyte supernatants compared to those from unstimulated monocytes (FIG. 7A). These data demonstrated that the initial release of PAF occurring within 30–60 minutes of exposure to DDAVP is followed by a period in which PAF secretion is decreased or ceases to occur. This suggests that the PAF secreted earlier is removed from the supernatant media by association with the monocyte surface. This hypothesis would be consistent with the subsequent rise in PAF secretion from monocytes observed at 6 hours since PAF-treated monocytes can be induced to release additional PAF (Prescott et al. 41990) Proc. Natl Acad. Sci. U.S.A. 81:3534–3538). Alternatively, PAF that has previously associated with monocytes following initial secretion may be released again into the supernatant.

Figure 7B:
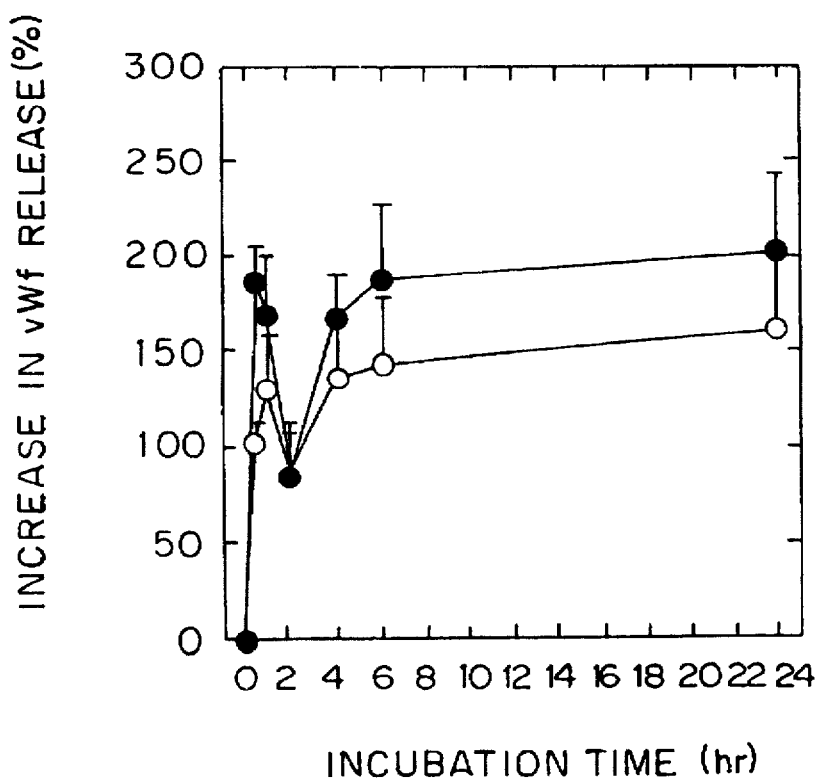

In order to show that the PAF detected in the RIA was bioactive regardless of the time of secretion from monocytes, aliquots of the same monocyte supernatants were then added to EC cultures for 4 hours at 37° C. and the release of vWf from ECs was determined. As shown in FIG. 7B, an increase in vWf release was observed at all time points. There were consistently higher levels of vWf released from ECs incubated with supernatants from DDAVP-stimulated monocytes as compared to unstimulated monocytes (except at 2 hours). In addition, the pattern of vWf released from ECs reflected the release of PAF secreted by monocytes (FIG. 7A,B).

EXAMPLE 6

Effect of PAF Antagonism on the Release of vWf from ECs

To confirm that DDAVP stimulated the secretion of PAF from monocytes, we studied the effect of the PAF receptor antagonist BTP-dioxolane on the release of vWf from ECs. It was established that if BTP-dioxolane was preincubated for 10 minutes with the ECs at a final concentration of 10 μM and the monocyte supernatants or other test solutions were made to this same concentration prior to incubation with the ECs, effective inhibition of the PAF-dependent release of vWf could be demonstrated. The following procedure was followed. The PAF receptor antagonist (±) trans-2,5-Bis(3, 4,5-trimethoxyphenyl)-1,3-dioxolane, or BTP-dioxolane (GIBCO BRL, Gaithersburg, Md.) was prepared as suggested by the manufacturer. This antagonist's specificity has been previously documented (Hwang et al., (1985) J. Biol. Chem. 260:15639–15645; Corey et al. (1987) J. Am. Chem. Soc. 109:7925–7926; (1988) Tetrahedron Letters 29:2899–2902; Ponpipom et al. (1988) Biochem. Biophys. Res. Commun. 150:1213–1220).

As shown in Table 3, BTP-dioxolane inhibited the release of vWf from ECs by 68% (P<0.005) when ECs were exposed to supernatants from untreated monocytes and by 82% (P<0.001) when they were exposed to supernatants from monocytes treated with 100 ng DDAVP/mL. Significant inhibition (75–83%) of the effects of 100 pM (P<0.001) or 300 pM PAF (P<0.005) on vWf release from ECs was observed in the presence of BTP-dioxolane. Release of vWf from ECs was slightly inhibited by 15% (P<0.025) when thrombin, an agent known to promote PAF synthesis and release (Whatley et al. (1990) J. Biol. Chem. 265:15550–59), was used to stimulate the ECs.

EXAMPLE 7

Effect of Supernatants from DDAVP-Treated Monocytes on PGI$_2$ Release from ECs

ECs have been shown by other investigators to release PGI$_2$ in response to stimulation with PAF (D'Humieres et al. (1986) Eur. J. Pharmacol. 131:13–19). Since we have shown that increased levels of PAF secreted by monocytes treated with DDAVP caused an increase in the release of vWf from ECs, we wished to determine if PGI$_2$ release from ECs was also enhanced. The results indicate that an increase in PGI$_2$ release from ECs occurred when they were incubated with supernatants from DDAVP-treated rather than from untreated monocytes (538±136 cf. 332±107 pg/mL). These data are corrected for the amount of PGI2 secreted by the untreated or DDAVP-treated monocytes and present in the supernatants prior to incubation with the ECs. If the data are expressed as a percentage increase in PGI$_2$ released from ECs exposed to supernatants from DDAVP-treated compared to untreated monocytes, in order to control for variability in the basal response between the various monocyte and EC preparations, a 60% increase in PGI$_2$ release was observed (P<0.05).

The mechanism by which DDAVP enhances the release of von Willebrand factor as well as factor VIII from their storage sites has been the subject of investigations for many years. The above results show that PAF can directly stimulate the release of von Willebrand factor from endothelial cells and that DDAVP treatment of monocytes results in the secretion of PAF.

Figure 6:
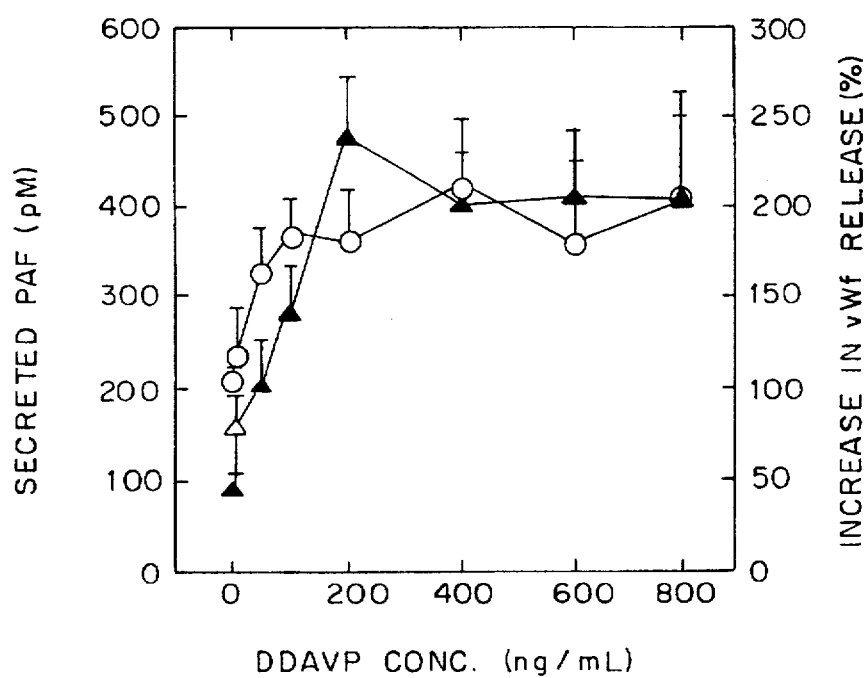
FIG. 6 shows the effect of DDAVP concentration on the secretion of PAF (▲) and von Willebrand factor (○) releasing factor from monocytes ((n=5 or more experiments). Monocytes ($10^8$/mL) were incubated with 0–800 ng DDAVP/mL (0–676 nM) for 30 minutes. After removal of the monocytes by centrifugation, the PAF contents were determined by RIA as described in Materials and Methods. In addition, alilquots of the same supernatants were incubated with ECs for a period of 4 hours. The vWf released from ECs was determined by an ELISA as described in Materials and Methods. Statistical analyses: ANOVA for the effect of DDAVP concentration on PAF secretion from monocytes (F=6.44, P<0.001) and monocyte conditioned media on vWF release from ECs (F=3.20, P<0.005).

Several pieces of evidence support the involvement of increased PAF release from DDAVP-stimulated monocytes with the observed enhancement of vWf release from ECs. Enhancement of vWf release from ECs following exposure to the supernatants of DDAVP-treated monocytes was only observed when the levels of PAF, determined by a highly specific and sensitive assay, increased above that observed in the media recovered from ECs exposed to supernatants from untreated monocytes (FIG. 1). In addition, as the level of PAF in the supernatants secreted from DDAVP-treated monocytes increased, the degree of enhancement in vWf release from ECs exposed to these supernatants also increased (FIG. 2). Furthermore, exposure of ECs to reconstituted lipid extracts of supernatants from untreated and DDAVP-treated monocytes produced similar vWf release compared to their unextracted counterparts (FIG. 3). Stimulation of vWf release from ECs in a dose-dependent (FIG. 4) and time-dependent manner (FIG. 5) could be shown when a commercial PAF preparation was added to EC cultures. Above 150 pM, PAF released from monocytes appears to further stimulate vWf release from ECs (FIG. 2) unlike the results obtained with the synthetic form of PAF. This suggests that once this level of PAF is attained, other factors may be secreted from monocytes that further contribute to the observed enhancement in vWf release. The secretion of PAF from monocytes was both DDAVP dose-dependent (FIG. 6) and time-dependent (FIG. 7). Confirmation of the involvement of PAF in vWf release from ECs was obtained from the effect of the specific PAF-receptor antagonist BTP-dioxolane, which blocked vWf release from ECs treated with either purified PAF or with the PAF present in supernatants from monocytes treated with or without DDAVP (Table 3). Although a small effect of the BTP-dioxolane on vWf release was observed with thrombin-treated ECs, this can be explained from the known effect of thrombin on the synthesis and secretion of PAF directly by ECs (Snyder, 1990). Our study clearly demonstrates that the treatment of the ECs with PAF enhances the release of vWf from ECs. Thus, enhanced PAF secretion by monocytes is one mechanism whereby DDAVP can induce vWf release from human ECs. The specificity of the RIA indicates that the $C_{16}$ and $C_{18}$ alkyl moieties of PAF have been secreted from monocytes.

In conclusion, the above results show that PAF added directly to endothelial cells can induce the release of von Willebrand factor and further that DDAVP treatment of monocytes results in a secretion of PAF in a dose and time dependent manner. Therefore, enhanced secretion of PAF, which serves as an intermediary, by monocytes is one mechanism by which DDVAP induces the release of von Willebrand factor from human endothelial cells. The stimulated release of von Willebrand factor induced by PAF appears to be specific since it is inhibited by a PAF receptor antagonist. Although PAF is known to be involved in various haemostatic, inflammatory and immune response functions, we have discovered a previously undocumented function of PAF, namely the haemostatic effect of PAF in regulating the release of von Willebrand factor from endothelial cells.

It should be noted that all of the data were evaluated using standard statistical methods for the determination of the means and standard error of the means (SEM), one-way analysis of variance (ANOVA), correlation coefficients, and the levels of significance between the paired means using the Student's t-test. The figures were plotted on an HP III laser printer using Sigmaplot 4.0 software (Jandel Scientific, Corte Madera, Calif.).

Release of Factor VIII

It is well established that DDAVP stimulates the release of not only von Willebrand factor but also of factor VIII (Bolan et al. (1990) supra; Ghirardini et al. (1987) Thromb. Haemost. 58:896–898; MacGregor et al. (1988) Thromb. Haemost. 59:34–39; Rodeghiero et al. (1991) Blood Reviews 5:155–161; Mannucci (1988) Blood 72: 1449–1455; Mannucci (1986) Progress Hemostas. Thromb. 8:19–45). It is also known that von Willebrand factor circulates as a noncovalent complex with factor VIII (Rodeghiero et al. (1991) supra; Weiss et al. (1977) Stabilization of Factor VIII in Plasma by von Willebrand factor, Journal of Clinical Investigation 60: 390 to 401). Given that the above studies established that PAF is the intermediary through which DDAVP and its analogues effect its mechanism of action, the injection of PAF would also cause the release of factor VIII. Similarly, it is contemplated that any analogues or derivatives of PAF would also cause the release of von Willebrand factor and factor VIII. Similarly, it is also contemplated that any compounds which stimulate the release of PAF would cause the release of vWf and Factor VIII and accordingly fall within the scope of the present invention.

While reference is made throughout the specification to DDAVP, it should be noted that there also exists a number of AVP (arginine vasopressin) analogues and DDAVP analogues having the same effect as DDAVP.

While the present invention has been described in connection with a specific embodiment thereof, various modifications will occur to those skilled in the art without departing from the spirit and scope of the invention as set forth in the appended claims. By way of example, while the disclosure pertains only to the use of PAF, it will be apparent to one skilled in the art that any analogues or derivatives of PAF having PAF-like activity will also fall within the scope of the present invention as will any compounds stimulating the release of PAF. Furthermore, it will be apparent that PAF can be used not only for the treatment of von Willebrand disease or haemophilia A but can also be used in normal blood donors for plasma fractionation purposes or in patients to increase their levels of factor VIII and von Willebrand factor. We therefore wish to embody within the scope of the patent which may be granted hereon all such embodiments as reasonably and properly fall within the scope of our contribution to the art.

TABLE 1

Effect of DDAVP on the secretion of vWf releasing factor and monocycle cytokines[1]

| Monocyte product secreted | DDAVP concentration | | | |
|---|---|---|---|---|
| | 0 ng/mL | 100 ng/mL | P-value | n |
| vWf releasing factor (%) | 131 ± 15 | 234 ± 35 | P <0.05 | 6 |
| IL-1β (pg/mL) | 319 ± 118 | 271 ± 93 | N.S. | 6 |
| IL-6 (pg/mL) | 23 ± 9 | 26 ± 2 | N.S. | 6 |
| TNF-α (pg/mL) | 4 ± 3 | 0 ± 0 | N.S. | 6 |
| GM-CSF (pg/mL) | 0 ± 0 | 0 ± 0 | N.S. | 6 |
| G-CSF (pg/mL) | 0 ± 0 | 0 ± 0 | N.S. | 6 |
| vWf releasing factor (%) | 147 ± 29 | 291 ± 58 | P <0.05 | 12 |
| Il-8 (pg/mL) | 690 ± 257 | 639 ± 214 | N.S. | 12 |

[1]Monocytes were incubated with (100 ng/mL or 84.5 nM) or without (0 ng/mL) DDAVP for 30 minutes, and the conditioned media were then assayed for the secreted cytokine products by ELISA as indicated in Materials and Methods. The product responsible for enhancing the release of vWf from ECs, termed vWf releasing factor, was determined from its effect in promoting vWf release following incubation of the monocyte conditioned media with ECs for 4 hours. Released vWf was assessed by ELISA of the EC conditioned media as described in Materials and Methods.

TABLE 2

Effect of DDAVP on the secretion of vWf releasing factor, prostaglandins, and adenine nucleotides from monocytes[1]

| Monocyte product secreted | DDAVP concentration | | | |
|---|---|---|---|---|
| | 0 ng/mL | 100 ng/mL | P-value | n |
| vWf releasing factor (%) | 122 ± 16 | 307 ± 62 | P <0.01 | 10 |
| PGE$_2$ (pg/mL) | 3.61 ± 0.80 | 4.37 ± 1.70 | N.S. | 10 |
| PGF$_{2\alpha}$ (pg/mL) | 333 ± 116 | 406 ± 124 | N.S. | 5 |
| vWf releasing factor (%) | 153 ± 35 | 347 ± 66 | P <0.05 | 9 |
| PGI$_2$ (pg/mL) | 106 ± 17 | 107 ± 18 | N.S. | 9 |
| vWf releasing factor (%) | 99 ± 17 | 211 ± 33 | P <0.025 | 6 |

TABLE 2-continued

Effect of DDAVP on the secretion of vWf releasing factor, prostaglandins, and adenine nucleotides from monocytes[1]

| Monocyte product secreted | DDAVP concentration | | | |
|---|---|---|---|---|
| | 0 ng/mL | 100 ng/mL | P-value | n |
| ATP (nM) | 10.3 ± 6.6 | 7.4 ± 4.4 | N.S. | 6 |
| ADP (nM) | 16.8 ± 5.5 | 17.6 ± 12.2 | N.S. | 5 |

[1]Monocytes were incubated with (100 ng/mL or 84.5 nM) or without (0 ng/mL) DDAVP for 30 minutes, and the conditioned media were then assayed for the indicated prostaglandins and adenine nucleotides as described in Materials and Methods. The product responsible for enhancing the release of vWf from ECs, termed vWf releasing factor, was determined from its effect in promoting vWf release following incubation of the monocyte conditioned media with Ecs for 4 hours. Released vWf was assessed by ELISA of the EC conditioned media as described in Materials and Methods.

TABLE 3

Effect of BTP-dioxolane on the release of vWf from ECs exposed to condiitoned media from untreated or stimulated monocytes[1]

| Agonist | Conc. | Increase in vWf release (%) | | % Inhibition |
|---|---|---|---|---|
| | | BTP-dioxolane absent | BTP-dioxolane present | |
| DDAVP | 0 ng/mL | 92.6 ± 14.7%$^a$ | 29.3 ± 10.6$^b$ | 68.4 ± 10.4%$^c$ |
| | 100 ng/mL | 197.2 ± 22.8%$^d$ | 35.9 ± 12.4%$^e$ | 81.8 ± 7.0%$^f$ |
| PAF | 100 pM | 190.8 ± 46.6%$^g$ | 48.2 ± 12.4%$^h$ | 74.7 ± 4.0%$^f$ |
| | 300 pM | 204.2 ± 48.7%$^j$ | 34.3 ± 32.3%$^k$ | 83.2 ± 11%$^l$ |
| Thrombin | 5 U/mL | 123.5 ± 11.3$^m$ | 105.4 ± 21.2%$^n$ | 14.7 ± 4.0%$^o$ |

[1]Conditioned media from monocytes left untreated (0 ng/mL) or treated with DDAVP (100 ng/mL or 85.4 nM) for 30 minutes were incubated with ECs for 4 hours in the absence or presence of BTP-dioxolane (10 μM) as described in Materials and Methods. Alternatively, ECs were incubated with fresh media containing either 100 or 300 pM PAF or 5 units/mL of thrombin for 4 hours. The release of vWf was assessed in the recovered EC conditioned media by ELISA. The % inhbition of vWf release was computed as: 100% - (% increase in vWf release with/without BTP-dioxolane × 100%) Statistical analysis (paired t-test) for DDAVP: a vs. b (P <0.005), a vs. d (P <0.01), d vs. e (P <0.001), c (P <0.005), f (P <0.001), PAF: g vs. h (P <0.001), j vs. k (P <0.01), i (P <0.001), l (P <0.005) and thrombin: 0 (P <0.025) (n = 5).

We claim:

1. A method for stimulating the release of von Willebrand factor and/or Factor VIII in human cells comprising administering to said human cells a compound selected from the group consisting of platelet activating factor (PAF) having the following formula:

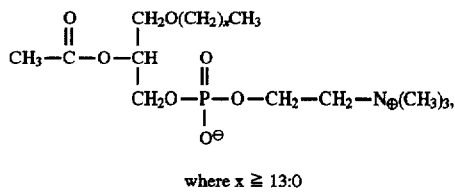

where x ≧ 13:0 and an analogue or derivative of PAF having PAF activity in an amount effective to stimulate the release of von Willebrand factor and/or Factor VIII in human cells.

2. The method of claim 1 wherein PAF is administered to stimulate the release of von Willebrand factor.

3. The method of claim 1 wherein said analogue or derivative of PAF having PAF activity is administered to stimulate the release of von Willebrand factor.

4. The method of claim 1 wherein PAF is administered to stimulate the release of Factor VIII.

5. The method of claim 1 wherein said analogue or derivative of PAF having PAF activity is administered to stimulate the release of Factor VIII.

6. A method for treating von Willebrand disease comprising administering to a subject in need thereof a compound selected from the group consisting of platelet activating factor (PAF) having the following formula:

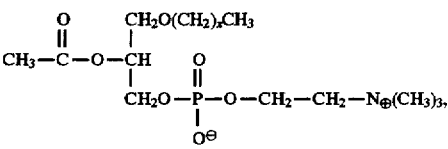

where x ≧ 13:0 and an analogue or derivative of PAF having PAF activity in an amount effective in stimulating the release of von Willebrand factor.

7. The method of claim 6 wherein PAF is administered to said subject.

8. The method of claim 6 wherein said analogue or derivative of PAF having PAF activity is administered to said subject.

9. A method of treating hemophilia A comprising administering to a subject in need thereof a compound selected from the group consisting of platelet activating factor (PAP) having the following formula:

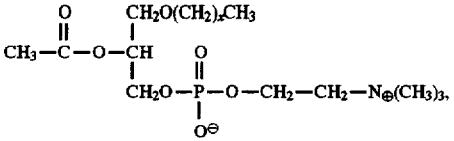

where x ≧ 13:0 and an analogue or derivative of PAF having PAF activity in an amount effective in stimulating the release of Factor VIII.

10. The method of claim 9 wherein PAF is administered to said subject.

11. The method of claim 9 wherein said analogue or derivative of PAF having PAF activity is administered to said subject.

12. A pharmaceutical composition comprising a compound selected from the group consisting of platelet activating factor (PAF) having the following formula:

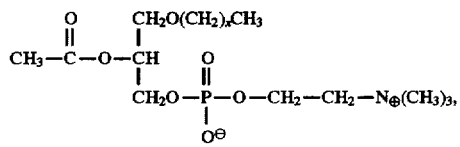

where x ≧ 13:0 and an analogue or derivative of PAF having PAF activity in an amount effective in stimulating the release of von Willebrand factor and/or Factor VIII in human cells, wherein said human cells are exposed to a concentration in the range of about 25 to 300 picomolar of said compound, and a pharmaceutically acceptable carrier.

13. The pharmaceutical composition of claim 12 which comprises an amount of PAF effective in stimulating the release of von Willebrand factor.

14. The pharmaceutical composition of claim 12 which comprises an amount of said analogue or derivative of PAF having PAF activity effective in stimulating the release of von Willebrand factor.

15. The pharmaceutical composition of claim 12 which comprises an amount of PAF effective in stimulating the release of Factor VIII.

16. The pharmaceutical composition of claim 12 which comprises an amount of said analogue or derivative of PAF having PAF activity effective in stimulating the release of Factor VIII.

* * * * *

UNITED STATES PATENT AND TRADEMARK OFFICE
CERTIFICATE OF CORRECTION

PATENT NO.   : 5,631,246
DATED        : May 20, 1997
INVENTOR(S)  : Hashemi et al.

Page 1 of 3

It is certified that error appears in the above-indentified patent and that said Letters Patent is hereby corrected as shown below:

COLUMN 1:

Line 5, delete "yon" and insert therefor --von--;

line 12, delete "Witlebrand" and insert therefor --Willebrand--;

line 17, delete "the.";

line 33, delete "yon" and insert therefor --von--.

COLUMN 2:

Line 5, delete "Will" and insert therefor --Wille--;

COLUMN 2:

line 6, delete "ebrand" and insert therefor --brand--;

line 11, delete "yon" and insert therefor --von--;

lin 12, delete "verus" and insert therefor --versus--;

line 21, delete "Monolayers" and insert therefor --Monolayer--;

line 22, delete "Pm" and insert therefor --pM--;

line 39, delete "alilquots" and insert therefor --aliquots--.

COLUMN 5:

Line 2, delete "c." and insert therefor --C--;

line 50, delete "c." and insert therefor --C--.

UNITED STATES PATENT AND TRADEMARK OFFICE
CERTIFICATE OF CORRECTION

PATENT NO. : 5,631,246
DATED : May 20, 1997
INVENTOR(S) : Hashemi et al.

Page 2 of 3

It is certified that error appears in the above-indentified patent and that said Letters Patent is hereby corrected as shown below:

COLUMN 6:

Line 5, delete "3xin" and insert therefor --3 x in--;
line 18, delete "C." and insert therefor --C--;
line 20, delete "C." and insert therefor --C--;
line 46, delete "68°C." and insert therefor --68°C--;
line 46, delete "80°C." and insert therefor --80°C--;

COLUMN 8:

Line 13, delete "Cla " and insert therefor --$C_{18}$--;
line 14, delete "C." and insert therefor --C--;
line 39, delete "pico molar" and insert therefor --picomolar--;
line 40 delete "C." and insert therefor --C--;
line 41 insert after "of" --vWf from ECs--.

COLUMN 9:

Line 10, delete "C." and insert therefor --C--;
line 41, delete "C." and insert therefor --C--.

COLUMN 12:

Table 1, line 30, delete "monocycle" and insert therefor --monocyte--.

UNITED STATES PATENT AND TRADEMARK OFFICE
CERTIFICATE OF CORRECTION

PATENT NO. : 5,631,246
DATED : May 20, 1997
INVENTOR(S) : Hashemi et al.

It is certified that error appears in the above-indentified patent and that said Letters Patent is hereby corrected as shown below:

COLUMN 13:

Table 3, second line of title, delete "conditoned" and insert therefor --conditioned--.

Table 3, third line, under "% Inhibition" delete "74.7±4.0%$^f$" and insert therefor --74.7±4.0%$^i$--.

Table 3, ninth line of footnote 1, delete "O" and insert therefor --o--.

Signed and Sealed this

Twenty-third Day of September, 1997

Attest:

Attesting Officer

BRUCE LEHMAN

Commissioner of Patents and Trademarks